(12) United States Patent
Loewenberg et al.

(10) Patent No.: US 6,177,584 B1
(45) Date of Patent: Jan. 23, 2001

(54) PROCESS FOR NEUTRALIZING AND REDUCING RESIDUAL HALOGEN CONTENTS IN ALKOXYSILANES OR ALKOXYSILANE-BASED COMPOSITIONS

(75) Inventors: Peter Loewenberg; Frank Kropfgans, both of Rheinfelden; Ralf Laven, Schwoerstadt; Roland Edelmann, Wehr; Albert-Johannes Frings, Rheinfelden; Michael Horn, Rheinfelden; Peter Jenkner, Rheinfelden; Helmut Mack, Rheinfelden; Jaroslaw Monkiewicz, Rheinfelden; Burkhard Standke, Loerrach, all of (DE)

(73) Assignee: Degussa-Huels Aktiengesellschaft, Frankfurt (DE)

( * ) Notice: Under 35 U.S.C. 154(b), the term of this patent shall be extended for 0 days.

(21) Appl. No.: 09/427,118

(22) Filed: Oct. 26, 1999

(30) Foreign Application Priority Data

Oct. 26, 1998 (DE) .............................................. 198 49 196

(51) Int. Cl.$^7$ ........................................................ C07F 7/08
(52) U.S. Cl. .............................................................. 556/466
(58) Field of Search ................................................ 556/466

(56) References Cited

U.S. PATENT DOCUMENTS

| | | | | |
|---|---|---|---|---|
| 5,104,999 | * | 4/1992 | Satoh | 446/466 |
| 5,210,254 | * | 5/1993 | Ritscher et al. | 556/466 |
| 5,260,470 | * | 11/1993 | Goebel et al. | 556/466 |

* cited by examiner

*Primary Examiner*—Paul F. Shaver
(74) *Attorney, Agent, or Firm*—Oblon, Spivak, McClelland, Maier & Neustadt, P.C.

(57) ABSTRACT

The present invention relates to a process for neutralizing and reducing the residual halogen content in alkoxysilanes and alkoxysilane-based compositions, which includes treating an alkoxysilane having a residual content of acidic halide, or a corresponding alkoxysilane-based composition, with metallic magnesium in the presence of an alcohol and separating off the resulting solids.

18 Claims, No Drawings

PROCESS FOR NEUTRALIZING AND REDUCING RESIDUAL HALOGEN CONTENTS IN ALKOXYSILANES OR ALKOXYSILANE-BASED COMPOSITIONS

BACKGROUND OF THE INVENTION

1. Field of the Invention

The present invention relates to a process for neutralizing and reducing the residual halogen content in alkoxysilanes or alkoxysilane-based compositions.

2. Discussion of the Background

Alkoxysilanes and alkoxysilane-based compositions are used in many areas as adhesion promoters, crosslinkers in polymers, as release agents, as additives in paints and coatings, for rendering surfaces hydrophobic, for textiles and leather, protecting buildings and facades, book conservation, modification of surface properties, coating glass fibers or silanizing filters and pigments, and also for improving the Theological properties of polymer dispersions and emulsions.

Alkoxysilanes are generally prepared using halosilanes, and particularly chlorosilanes. For example, reacting chloropropyltrichlorosilane with methanol produces a chloropropyltrimethoxysilane with the elimination of HCI. Residual halogen content, i.e. residues of acidic or hydrolyzable chloride, can remain in the alkoxysilane, even after purification of the product by distillation. In addition, residual amounts of nonhydrolyzable chlorine can also remain in the product, for example, in the preparation of aminoalkylalkoxysilanes, due to unreacted starting materials such as chloroalkylalkoxysilanes.

Attempts are currently being made to prepare alkoxysilanes and products which contain alkoxysilanes (e.g. EP 0 273 867 B1, DE 27 51 714 C2) and alkoxysilane-based compositions (for example, EP 0 049 365 A2, EP 0 518 057 A1, EP 0 675 128 A1, EP 0 716 127 A2 or EP 0 716 128 A2, possible, particularly acidic or hydrolyzable chlorides. An essential product characteristic is color, and Gardner/APHA color indexes, as specified in ISO 6271, that are as low as possible are being sought.

It is known to remove the residual halogen content from alkoxysilanes by reacting or neutralizing the residual halogen content with alkali metal alkoxides, such as sodium methoxide, and separating off the resulting salt (EP 0 282 846 A2, EP 0 741 137 A1). Neutralization processes of this type have the disadvantage that considerable amounts of product are also decomposed in the reaction. Decomposition products include siloxanes, tetralkoxysilane, and addition products such as methoxyethyltrimethoxysilanes by reaction of sodium methoxide and vinyltrimethoxysilane, methoxypropyl-trimethoxysilane formed from sodium ethoxide and chloropropyltrimethoxysilane, methoxypropylmethyl-dimethoxysilanes from sodium methoxide and chloropropylmethyldimethoxysilane, or, in the case of the reaction of alkali metal methoxide and an alkyltrimethoxysilane, the highly toxic tetramethoxysilane.

In addition, when the usual neutralizing agents, such as alkali metal alkoxides, are used, the color index of the treated alkoxysilane is frequently impaired.

The publications, CN 11 07 85 1A and 11 07 85 2 A, describe processes for preparing vinyl-triethoxysilane and chloropropyltrimethoxysilane, which are said to provide very pure products by using magnesium alkoxides. The disadvantage of these processes is that the magnesium alkoxides, being highly moisture-sensitive products, are difficult to handle. Furthermore, magnesium alkoxides are present in powder form and have a tendency to form lumps, which again makes it difficult to meter the magnesium alkoxide exactly. This disadvantage particularly affects the metering into heated or hot products, which is usually carried out in practice, because the silane and other volatile constituents of the reaction preparation condense on the magnesium alkoxides, partially dissolving them and thus converting them into a form no longer flows.

To avoid the above-noted disadvantage, attempts have been made to use alcoholic solutions of the magnesium alkoxides. However, such attempts are burdened by the problem that considerable amounts of alcohol are added in the neutralization step and must be separated off again by distillation, which requires both time and energy. In addition, the magnesium alkoxides are highly expensive and are available only with restrictions in industrial amounts.

SUMMARY OF THE INVENTION

One object of the present invention therefore is to provide a process, which reduces the acidic residual halogen content and neutralizes alkoxysilanes or alkoxysilane-based compositions as effectively as possible and as gently to the product as possible, using starting products which are sufficiently available commercially and inexpensive.

Another object of the invention is to provide a process that neutralizes and reduces the amount of acidic residual halides, particular chloride, in alkoxysilanes or alkoxysilane-based compositions in simple, economic, gentle and effective manner.

These and other objects are achieved according to the invention, the first embodiment of which relates to a process for neutralizing and reducing the residual halogen content in alkoxysilanes or in alkoxysilane-based compositions, and includes:

treating an alkoxysilane comprising an acidic halide, or treating an alkoxysilane-based composition containing an acidic halide, with metallic magnesium in the presence of an alcohol, to produce a product mixture; and separating a solid from the product mixture.

Another embodiment of the present invention relates to an alkoxysilane or alkoxysilane-based composition prepared by the above process and which includes less than 10 ppm acidic halide by weight.

BRIEF DESCRIPTION OF THE PREFERRED EMBODIMENTS

Various other objects, features and attendant advantages of the present invention will be more fully appreciated as the same becomes better understood from the following detailed description of the preferred embodiments.

Surprisingly, it has been found that alkoxysilanes or alkoxysilane-based compositions which have a residual content of acidic halide, e.g. acidic chloride are neutralized by adding metallic magnesium in the presence of small amounts of alcohol without the expected side reactions, e.g. the occurrence of a Grignard synthesis. What is more surprising is the particularly gentle action toward the products of the reaction, which, even under more drastic conditions such as elevated temperatures and long reaction times, does not lead to the formation of new byproducts. The solid content that is present in the product after the neutralization step, i.e. metallic magnesium and resulting magnesium chloride, can be separated off in a simple manner, e.g. by filtration. In this case, products are advantageously obtained whose residue halogen content, in particular residual chloride content, are drastically reduced. Small amounts of alcohol in the product, e.g. up to 5% by weight generally do not interfere, but may be optionally removed by distillation.

More surprisingly, the color index of the alkoxysilanes and alkoxysilane-based compositions treated according to the invention is not impaired.

The present invention thus relates to a process for neutralizing and reducing the residual halogen content in alkoxysilanes or in alkoxysilane-based compositions, which includes treating an alkoxysilane which has a residual content of acidic halide, or a corresponding alkoxysilane-based composition, with metallic magnesium in the presence of an alcohol and subsequently separating off the solids present.

Preferably, the residual acidic halides are hydrolyzable, and they include acid chloride compounds such as hydrogen chloride, chlorosilanes, organofunctional chlorosilanes, chloroalkoxysilanes, and mixtures thereof.

Preferably, the treatment according to the invention is carried out by metering in magnesium, preferably in the form of turnings or powder, into the alkoxysilane or into the alkoxysilane-based composition, and optionally adding a little alcohol and subsequently heating the mixture.

Preferably, commercial magnesium turnings from Eckhart Non Ferrum (St. Georgen/A) of the "Eckhart 100" or "Almamet 150" type can be used. Preferably, magnesium powder or magnesium turnings are used with the average particle size being from 20 µm to 15 mm, particularly preferably from 50 µm to 10 mm, and very particularly preferably from 100 µm to 1 mm. However, other magnesium variants are also preferable, e.g. bars or ribbon.

Preferably, magnesium is used in excess, based on the halide. Preferably, it is added in a 100% excess, more preferably in a 150% excess, and most preferably in a 200% excess, based on the halide. Prior to the addition of the magnesium, the alkoxysilane to be treated can be admixed with an alcohol, for example methanol, ethanol, isopropanol, methoxyethanol or butanol and mixtures thereof. Preferably, the alcohol is present in the alkoxysilane which corresponds to the alkoxide of the alkoxysilane to be treated. Preferably, if small amounts of alcohol are present in the alkoxysilane, a solvent can be added, for example aliphatic or aromatic hydrocarbons, ethers or ketones, which is most preferably removed again from the alkoxysilane after the treatment. However, alcohol can also be added in excess.

It is generally preferred to add alcohol in small amounts, particularly preferably in an amount which is just sufficient to react with excess magnesium to completion to form magnesium alkoxide. Preferably the molar ratio of the added alcohol to the excess magnesium is greater than or equal to 2:1 to the molar amount of the excess magnesium, more preferably 2.5:1, and most preferably 3:1.

In a suitable manner, the alcohol content in the alkoxysilane to be treated is between 0.001 and 50% by weight, preferably between 0.01 and 30% by weight, particularly preferably between 0.1 and 20% by weight, very particularly preferably between 0.3 and 10% by weight, in each case based on the weight of the alkoxysilane.

Preferably, in the process according to the invention, the treatment is carried out in a temperature range from 0 to 200° C., preferably from 10 to 160° C., particularly preferably from 20° C. and the boiling point of the corresponding alkoxysilane.

In the process according to the invention, the treatment is preferably carried out under pressure. The range from 0.02 to 100 kPa is especially preferred.

In the process according to the invention, a treatment period between 1 minute and 16 hours is preferred, more preferably from 2 minutes to 4 hours, particularly preferably from 5 to 60 minutes, where good mixing likewise may be advantageous.

For further processing, the pure product, in particular alkoxysilanes treated according to the invention, for example vinyltrimethoxysilane, can be separated off from the product mixture by distillation. The product treated according to the invention can also be subjected to a separate distillation. Preferably, to separate off solid residues, the product mixture obtained after treatment according to the invention can be filtered. However, the separation can also be performed by centrifugation.

Preferably, in the process according to the invention the residual halide content, and particularly the content of acidic chloride, in the alkoxysilane is set to a value of <10 ppm by weight, more preferably <1 ppm by weight, i.e. in a suitable manner down to the detection limit. For example, by using the process according to the invention, the content of acidic chloride can be decreased from about 20,000 ppm by weight to a value <10 ppm by weight down to the detection limit. Preferably, in the process according to the invention at least a reduction of the content of acidic halide of more than 30% is achieved.

Preferred examples of alkoxysilanes or alkoxysilane-based compositions include vinyltrimethoxysilane, vinyltriethoxysilane, vinyl-tris(2-methoxyethoxy)silane, 3-chloropropyltrimethoxy-silane, 3-chloropropyltriethoxysilane, (3-chloropropyl)methyldimethoxysilane, (3-chloropropyl)methyldiethoxysilane, 3-aminopropyltrimethoxysilane, 3-aminopropyltriethoxysilane, (3-aminopropyl)methyldimethoxysilane. (3-aminopropyl)methyldiethoxysilane, (N-amino-3-aminopropyl)methyldimethoxysilane, Namino-ethyl-3-aminopropyl)methyldiethoxysilane 3-methacryl-oxypropyltrimethoxysilane. 3-methacryloxypropyltriethoxysilane and perfluoroalkyl- and fluoroalkyl-functional alkoxysilanes, such as 3,3,4,4,5,5,6,6,7,7,8,8,8-tridecafluoro -1,1,2,2-tetrahydrooctyltrimethoxysilane, 3,3,4,4,5,5,6,6,7,7,8,8,8-tridecafluoro-1,1,2,2-tetrahydro-octyltriethoxysilane, 3,3,4,4,5,5,6,6,7,7,8,8,9,9,10,10,10-heptadecafluoro-1,1,2,2-tetrahydrodecyltrimethoxysilane, 3,3,4,4,5,5,6,6,7,7,8,8,9,9,10,10,10-heptadecafluoro-1,1,2,2-tetrahydrodecyltriethoxysilane and compositions of oligomeric organoalkoxysiloxanes, e.g. those containing oligomeric vinylsiloxanes, such as DYNASYLAN®6490 which is prepared, starting from vinyltrimethoxysilane, by a specific condensation, or DYNASYLAN®6498 which is obtainable, starting from vinyltriethoxysilane, by specific condensation, and compositions containing oligomeric vinyllalkylsiloxanes such as DYNASYLAN®6598, as is given by, in particular, EP 0 518 957 A1, and compositions containing oligomeric alkylalkoxy-silanes, such as DYNASYLAN®9281, cf DE 196 24 032 A1, and also compositions of water-soluble, predominantly completely hydrolyzed organopolysiloxanes such as emerge, in particular, from EP 0 675 128 A1, EP 0 716 127 A2 and EP 0 716 128 A2 (the entire contents of each of the aforementioned references are hereby incorporated by reference) and mixtures thereof.

In particular, the use of the process according to the invention also makes possible in an advantageous and surprising manner the retention of existing good color indices of the alkoxysilanes or alkoxysilane-based compositions to be treated.

EXAMPLES

Having generally described this invention, a further understanding can be obtained by reference to certain specific examples which are provided herein for purposes of illustration only and are not intended to be limiting unless otherwise specified.

Comparison Example A 30 g of a 30% strength sodium methoxide solution are added to 3,000 g of vinyltrimethoxysilane having a hydrolyzable chloride content of 217 ppm by weight and a total chlorine content 231 ppm by weight and a Gardner color index of 1 in a jacketed flask. A dark yellow solution having a Gardner color index of 8 is obtained. The mixture is then distilled for a period of 4 hours. In the resulting distillate, the hydrolyzable chloride content of <1 ppm by weight and a tetramethoxysilane content of 600 ppm by weight are determined. In the dark-brown distillation residue, inter alia, as main constituent, the decomposition product methoxyethyl-trimethoxysilane is found.

Comparison Example B 112 g of a 30% strength sodium methoxide solution are added to 3,388 g of 3-chloropropyltrimethoxysilane having a hydrolyzable chloride content of approximately 6,740 ppm by weight and a content of high-boilers of approximately 3% in a jacketed flask. The mixture is then distilled for a period of 10 hours. In the resulting distillate, the hydrolyzable chloride content is determined to be 212 ppm by weight. The residue quantity increased to 11% by weight of high boilers, based on the total amount.

Comparison Example C 3 g of sodium methoxide powder are added to 100 g of 3-chloropropylmethyldimethoxysilane having a hydrolyzable chloride content of approximately 22,000 ppm by weight and a content of high-boilers of approximately 1% in a jacketed flask. The mixture is refluxed for a period of 15 hours. The content of high boilers is determined again. A value of 15% is found.

Comparison Example D 5 g of potassium tert-butoxide are added to 100 g of 3-chloropropylmethyldimethoxysilane having a hydrolyzable chloride content of approximately 22,000 ppm by weight and a content of high-boilers of approximately 1% in a jacketed flask. The mixture is refluxed for a period of 15 hours. The content of high boilers increases to 17%. Comparison Example E 168 g of a 20% strength sodium ethoxide solution are added to 3,500 g of chloropropyltriethoxysilane having a hydrolyzable chloride content of approximately 5,000 ppm by weight, a content of high boilers of approximately 2%, an ethanol content of approximately 3% and a Gardner color index of <1 in a jacketed flask and refluxed for a period of 2 hours. The mixture is then filtered. The hydrolyzable chloride content is determined to be 50 ppm by weight. An increase in high-boilers to approximately 12% is determined by gas chromatography. The Gardner color index is <4.

EXAMPLE 1

5 g of magnesium powder are added to 3,000 g of vinyltrimethoxysilane having a hydrolyzable chloride content of 400 ppm by weight, a total chlorine content of 416 ppm bv weight, a divinyltetranethoxydisiloxane content of approximately 1.5% by weight, of approximately 3% by weight of methanol and a Gardner color index of 1 in a jacketed flask. The magnesium reacts to form magnesium chloride. The color of the composition remains unchanged at a Gardner color index of 1. The mixture is then distilled for a period of 8 hours. In the resulting distillate, the hydrolyzable chloride content determined to be <1 ppm by weight and a tetramethoxysilane content of <100 ppm by weight is determined. The pale yellow distillation residue does not contain any additional amounts of divinyltetramethoxydisiloxane. Methoxyethyltrimethoxy-silane was not found.

EXAMPLE 2

16.2 g of magnesium powder (corresponding to an Mg excess of 100% based on chloride) are added to 3,500 g of 3-chloropropyltrimethoxysilane having a hydrolyzable chloride content of approximately 6,740 ppm by weight a content of high boilers of approximately 3% and a content of approximately 3% by weight methanol in a jacketed flask. The magnesium reacts to form magnesium chloride. The mixture is then distilled for a period of 8 hours. In the resulting distillate, the hydrolyzable chloride content is determined to be 38.3 ppm by weight. No increase in high boilers was observed.

EXAMPLE 3

66 g of magnesium turnings (type Almamet 150) (corresponding to a magnesium excess of 100%, based on chloride) are added to 3,500 g of 3-chloropropylmethyldimethoxysilane having a hydrolyzable chloride content of approximately 22,000 ppm by weight, a content of high boilers approximately 3% and a content of approximately 9% by weight methanol in a jacketed flask. The magnesium reacts to form magnesium chloride. The mixture is then distilled for a period of 8 hours. In the resulting distillate, the hydrolyzable chloride content is determined to be 20 ppm by weight. No increase in high boilers was observed.

EXAMPLE 4

17 g of magnesium turnings (type Eckhart 100) are added to 3,500 g of chloropropyltriethoxysilane having a hydrolyzable chloride content of approximately 5,000 ppm by weight, a content of high boilers of approximately 2%, an ethanol content of approximately 3% and a Gardner color index of <1 in a jacketed flask and refluxed for a period of 2 hours. The magnesium reacts to form magnesium chloride. The mixture is then filtered. The hydrolyzable chloride content is determined to be 50 ppm by weight. No increase in high boilers was observed. The Gardner color index is unchanged at <1.

Obviously, numerous modifications and variations of the present invention are possible in light of the above teachings. It is therefore to be understood that within the scope of the appended claims, the invention may be practiced otherwise than as specifically described herein.

This application is based on german patent application DE 19849196.4, filed Oct. 26, 1998, the entire contents of which are hereby incorporated by reference.

What is claimed is:

1. A process for neutralizing and reducing the residual halogen content in alkoxysilanes or in alkoxysilane-based compositions, comprising:

treating an alkoxysilane comprising an acidic halide, or
treating an alkloxysilane-based composition comprising an acidic halide, with metallic magnesium in the presence of an alcohol, to produce a product mixture; and separating a solid from the product mixture.

2. The process as claimed in claim 1, wherein the magnesium is in the form of turnings or powder.

3. The process as claimed in claim 1, wherein the magnesium is used in excess, based on the amount of the halide.

4. The process as claimed in claim 1, wherein the alcohol is added to the alkoxysilane prior to being treated with the magnesium.

5. The process as claimed in claim 1, wherein the alcohol is present in an amount of 0.001 to 50% by weight, based on the alkoxysilane.

6. The process as claimed in claim 1, wherein the alkoxysilane comprises an alkoxide group, and wherein the alcohol corresponds to the alkoxide in the alkoxide group.

7. The process as claimed in claim 1, wherein the treatment is carried out at a temperature of 0 to 200° C.

8. The process as claimed in claim 1, wherein the treatment is carried out under pressure.

9. The process as claimed in claim 1, wherein the treatment is carried out for a period of 1 minute to 16 hours.

10. The process as claimed in claim 1, wherein the residual halogen content is reduced or neutralized to a value of <10 ppm by weight, based on the alkoxysilane, to the detection limit.

11. The process as claimed in claim 1, wherein the halogen is chlorine.

12. The process as claimed in claim 2, wherein said powder or turnings have an average particle size of 20 $\mu$m to 15 mm.

13. The process as claimed in claim 3, wherein the magnesium is added in an excess of 100%, based on the amount of halogen.

14. The process as claimed in claim 4, further comprising adding a solvent to the alkoxysilane.

15. The process as claimed in claim 1, further comprising separating the treated alkoxysilane by distillation.

16. The process as claimed in claim 1, wherein said alkoxysilanes and alkoxysilane-based composition are independently selected from the group consisting of vinyltrimethoxysilane, vinyltriethoxysilane, vinyl-tris(2-methoxyethoxy)silane, 3-chloropropyltrimethoxy-silane, 3-chloropropyltriethoxysilane, (3-chloropropyl) methyldimethoxysilane, (3-chloropropyl)methyldiethoxysilane, 3-aminopropyltrimethoxysilane, 3-aminopropyltriethoxysilane, (3-aminopropyl) methyldimethoxysilane, (3-aminopropyl) methyldiethoxysilane, (N-amino-3-aminopropyl) methyldimethoxysilane, (Namino-ethyl-3-aminopropyl) methyldiethoxysilane 3-methacryloxypropyltrimethoxysilane. 3-methacryloxypropyltriethoxysilane and perfluoroalkyl- and fluoroalkyl-functional alkoxysilanes, such as 3,3,4,4,5,5,6,6,7,7,8,8-tridecafluoro-1,1,2,2-tetrahydrooctyltrimethoxysilane, 3,3,4,4,5,5,6,6,7,7,8,8-tridecafluoro-1,1,2,2-tetrahydrooctyltriethoxysilane, 3,3,4,4,5,5,6,6,7,7,8,8,9,9,10,10,10-heptadecafluoro-1,1,2,2-tetrahydrodecyltrimethoxysilane, 3,3,4,4,5,5,6,6,7,7,8,8,9,9,10,10,10-heptadecafluoro-1,1,2,2-tetrahydrodecyltriethoxysilane, oligomeric organoalkoxysiloxanes, oligomeric vinylsiloxanes, DYNASYLAN®6490, DYNASYLAN®6498, oligomeric vinyl/alkylsiloxanes, DYNASYLAN®6598, oligomeric alkylalkoxy-silanes, DYNASYLAN®9281, and watersoluble, predominantly completely hydrolyzed organopolysiloxanes, and mixtures thereof.

17. The process as claimed in claim 1, wherein said alcohol is selected from the group consisting of methanol, ethanol, isopropanol, methoxyethanol, and butanol, and mixtures thereof.

18. The process as claimed in claim 1, wherein said acidic halide is selected from the group consisting of hydrogen chloride, chlorosilanes, organofunctional chlorosilanes, and chloroalkoxy silanes, and mixtures thereof.

\* \* \* \* \*